(12) United States Patent
Verdine et al.

(10) Patent No.: US 8,691,534 B2
(45) Date of Patent: Apr. 8, 2014

(54) PREPARATION OF ROMIDEPSIN

(75) Inventors: Gregory L. Verdine, Newton, MA (US); Nicholas H. Vrolijk, Durham, NC (US); Stephan Bertel, Kundl (AT)

(73) Assignees: Celgene Corporation, Summit, NJ (US); Sandoz GmbH, Kundl (AT)

( * ) Notice: Subject to any disclaimer, the term of this patent is extended or adjusted under 35 U.S.C. 154(b) by 935 days.

(21) Appl. No.: 11/966,258

(22) Filed: Dec. 28, 2007

(65) Prior Publication Data

US 2009/0186382 A1    Jul. 23, 2009

Related U.S. Application Data

(60) Provisional application No. 60/882,698, filed on Dec. 29, 2006, provisional application No. 60/882,704, filed on Dec. 29, 2006.

(51) Int. Cl.
*C12P 21/04* (2006.01)

(52) U.S. Cl.
USPC .......................................................... 435/71.1

(58) Field of Classification Search
None
See application file for complete search history.

(56) References Cited

U.S. PATENT DOCUMENTS

| | | | |
|---|---|---|---|
| 4,977,138 A | 12/1990 | Okuhara et al. | |
| 5,605,793 A | 2/1997 | Stemmer | |
| 5,830,721 A | 11/1998 | Stemmer et al. | |
| 5,837,458 A | 11/1998 | Minshull et al. | |
| 6,117,679 A | 9/2000 | Stemmer | |
| 6,391,640 B1 | 5/2002 | Minshull et al. | |
| 6,403,555 B1 | 6/2002 | Skov et al. | |
| 6,548,479 B1 | 4/2003 | Skov et al. | |
| 6,706,686 B2 | 3/2004 | Long et al. | |
| 6,777,217 B1 | 8/2004 | Schreiber et al. | |
| 6,809,118 B2 | 10/2004 | Chung et al. | |
| 6,828,302 B1 | 12/2004 | Skov et al. | |
| 6,905,669 B2 | 6/2005 | DiMartino | |
| 6,946,441 B2 | 9/2005 | Long et al. | |
| 7,041,639 B2 | 5/2006 | Skov et al. | |
| 7,056,883 B2 | 6/2006 | Ito et al. | |
| 7,056,884 B2 | 6/2006 | Nakajima et al. | |
| 7,098,186 B2 | 8/2006 | Nagai et al. | |
| 7,314,862 B2 | 1/2008 | Naoe et al. | |
| 7,396,665 B2 | 7/2008 | Ueda et al. | |
| 7,470,722 B2 | 12/2008 | Malecha et al. | |
| 7,488,712 B2 | 2/2009 | Yoshida et al. | |
| 2003/0162293 A1 | 8/2003 | Chu et al. | |
| 2003/0186388 A1 | 10/2003 | Ueda et al. | |
| 2004/0018968 A1 | 1/2004 | Sgouros et al. | |
| 2004/0053820 A1 | 3/2004 | Nakajima et al. | |
| 2004/0072735 A1 | 4/2004 | Richon et al. | |
| 2004/0127523 A1 | 7/2004 | Bacopoulos et al. | |
| 2005/0070467 A1 | 3/2005 | Naoe et al. | |
| 2005/0159347 A1 | 7/2005 | DiMartino | |
| 2005/0187148 A1 | 8/2005 | Naoe et al. | |
| 2005/0187149 A1 | 8/2005 | Naoe et al. | |
| 2005/0191713 A1 | 9/2005 | Sasakawa et al. | |
| 2005/0222013 A1 | 10/2005 | Jung et al. | |
| 2005/0255532 A1 | 11/2005 | Ruben et al. | |
| 2005/0272647 A1 | 12/2005 | Yamaji et al. | |
| 2006/0018921 A1 | 1/2006 | Levenson et al. | |
| 2006/0019883 A1 | 1/2006 | Kronblad et al. | |
| 2006/0074124 A1 | 4/2006 | Napper et al. | |
| 2006/0100140 A1 | 5/2006 | Dent et al. | |
| 2006/0106049 A1 | 5/2006 | Odenike | |
| 2006/0128660 A1 | 6/2006 | Rajski et al. | |
| 2006/0135413 A1 | 6/2006 | Naoe et al. | |
| 2006/0223747 A1 | 10/2006 | Ito et al. | |
| 2006/0228404 A1 | 10/2006 | Anderson et al. | |
| 2006/0229237 A1 | 10/2006 | Chung et al. | |
| 2006/0229265 A1 | 10/2006 | Milburn et al. | |
| 2006/0270016 A1 | 11/2006 | Holm | |
| 2007/0110719 A1 | 5/2007 | Holm | |
| 2007/0129290 A1 | 6/2007 | Or et al. | |
| 2007/0148228 A1 | 6/2007 | Cumming et al. | |
| 2007/0292512 A1 | 12/2007 | Leonard et al. | |
| 2008/0214446 A1 | 9/2008 | Okada et al. | |
| 2008/0233562 A1 | 9/2008 | Sasakawa et al. | |
| 2009/0105130 A1 | 4/2009 | Toda et al. | |
| 2009/0105168 A1 | 4/2009 | Gruber et al. | |
| 2009/0105200 A1 | 4/2009 | Keegan et al. | |
| 2009/0105343 A1 | 4/2009 | Campbell et al. | |
| 2009/0131367 A1 | 5/2009 | Gore et al. | |

(Continued)

FOREIGN PATENT DOCUMENTS

| | | |
|---|---|---|
| CA | 2317003 | 8/2001 |
| EP | 0352646 | 7/1989 |

(Continued)

OTHER PUBLICATIONS (http://www.diaion.com/Sepabeads_Main/Sepabeads_Main_R_E.htm, accessed Aug. 18, 2009, last updated on Sep. 30, 2000).*
Sigma Product Information sheet (Sigma Product Information, Alumina, 1998).*
Finnin et al., *Nature*, 401:188-193, 1999.
Kahn et al. *J. Am. Chem. Soc.* 118:7237-7238, 1996.
Kisselev and Goldberg, "Proteasome inhibitors: from research tools to drug candidates" *Chem. Biol.* 8:739-58, 2001.
Nakajima et al., *Experimental Cell Res.* 241:126-133, 1998.
Piekarz et al. "A review of depsipeptide and other histone deacetylase inhibitors in clinical trials" *Curr. Pharm. Des.* 10:2289-98, 2004.
S. M. Berge, et al. J. Pharmaceutical Sciences, 66: 1-19, 1977.

(Continued)

*Primary Examiner* — Brian J Gangle
(74) *Attorney, Agent, or Firm* — Jones Day

(57) ABSTRACT

The invention provides an improved process for preparing romidepsin. The process involves producing, purifying, or storing romidepsin under conditions that prevent the formation of undesired adducts. Purifying romidepsin at an apparent pH lower than approximately 6.0 (e.g., between an apparent pH of 4.0 and 6.0) has been discovered to prevent the reduction of the disulfide bond of romidepsin and the subsequent formation of dimerized, oligomerized, or polymerized adducts. The invention also provides compositions of monomeric romidepsin free of dimerized, oligomerized, or polymerized adducts.

24 Claims, 1 Drawing Sheet

(56) References Cited

U.S. PATENT DOCUMENTS

| | | |
|---|---|---|
| 2009/0131390 A1 | 5/2009 | Ganesan et al. |
| 2009/0221473 A1 | 9/2009 | Chan et al. |
| 2009/0226431 A1 | 9/2009 | Habib |
| 2009/0264343 A1 | 10/2009 | Ueda et al. |
| 2009/0264439 A1 | 10/2009 | Dent et al. |
| 2009/0264617 A1 | 10/2009 | Ueda et al. |
| 2009/0270497 A1 | 10/2009 | Buggy |
| 2009/0285772 A1 | 11/2009 | Phiasivongsa et al. |
| 2009/0325156 A1 | 12/2009 | Figg et al. |
| 2009/0325867 A1 | 12/2009 | Cohen et al. |
| 2010/0034749 A1 | 2/2010 | Schulze et al. |
| 2010/0061984 A1 | 3/2010 | Greene et al. |

FOREIGN PATENT DOCUMENTS

| | | |
|---|---|---|
| EP | 1010705 | 6/2000 |
| EP | 1548026 | 8/2003 |
| EP | 1426054 | 6/2004 |
| JP | 1995-64872 | 7/1995 |
| JP | 11-335375 | 12/1999 |
| JP | 2001-348340 | 12/2001 |
| WO | WO 97/35990 | 10/1997 |
| WO | WO 98/40080 | 9/1998 |
| WO | WO 01/18171 | 3/2001 |
| WO | WO 01/42282 | 6/2001 |
| WO | WO-0206307 | 1/2002 |
| WO | WO-0215921 | 2/2002 |
| WO | WO-0220817 | 3/2002 |
| WO | WO-02055017 | 7/2002 |
| WO | WO-02055688 | 7/2002 |
| WO | WO 02/085400 | 10/2002 |
| WO | WO-02090534 | 11/2002 |
| WO | WO-03015810 | 2/2003 |
| WO | WO 03/024442 | 3/2003 |
| WO | WO-03017763 | 3/2003 |
| WO | WO-03035843 | 5/2003 |
| WO | WO-03053468 | 7/2003 |
| WO | WO-03070188 | 8/2003 |
| WO | WO-03083067 | 10/2003 |
| WO | WO-03084611 | 10/2003 |
| WO | WO-03088954 | 10/2003 |
| WO | WO-03103613 | 12/2003 |
| WO | WO-2004009771 | 1/2004 |
| WO | WO-2004017996 | 3/2004 |
| WO | WO-2004024160 | 3/2004 |
| WO | WO-2004062654 | 7/2004 |
| WO | WO-2004064727 | 8/2004 |
| WO | WO-2004074478 | 9/2004 |
| WO | WO-2004096289 | 11/2004 |
| WO | WO-2004098495 | 11/2004 |
| WO | WO-2005000282 | 1/2005 |
| WO | WO-2005000289 | 1/2005 |
| WO | WO-2005000332 | 1/2005 |
| WO | WO-2005009961 | 2/2005 |
| WO | WO-2005018578 | 3/2005 |
| WO | WO-2005023179 | 3/2005 |
| WO | WO-2005027842 | 3/2005 |
| WO | WO-2005030239 | 4/2005 |
| WO | WO-2005051430 | 6/2005 |
| WO | WO-2005052143 | 6/2005 |
| WO | WO-2005053609 | 6/2005 |
| WO | WO-2005058298 | 6/2005 |
| WO | WO-2005079827 | 9/2005 |
| WO | WO-2005085864 | 9/2005 |
| WO | WO-2005087206 | 9/2005 |
| WO | WO-2005105055 | 11/2005 |
| WO | WO-2005105066 | 11/2005 |
| WO | WO-2005115149 | 12/2005 |
| WO | WO-2005117930 | 12/2005 |
| WO | WO-2006027346 | 3/2006 |
| WO | WO-2006055621 | 5/2006 |
| WO | WO-2006060382 | 6/2006 |
| WO | WO-2006060429 | 6/2006 |
| WO | WO-2006129105 | 12/2006 |
| WO | WO-2007009539 | 1/2007 |
| WO | WO 2007/040522 | 4/2007 |
| WO | WO-2007040522 | 4/2007 |
| WO | WO-2007058896 | 5/2007 |
| WO | WO-2007061939 | 5/2007 |
| WO | WO-2007145704 | 12/2007 |
| WO | WO-2007146730 | 12/2007 |
| WO | WO-2008013589 | 1/2008 |
| WO | WO 2008/031820 | 3/2008 |
| WO | WO 2008/062201 | 5/2008 |
| WO | WO 2008/062232 | 5/2008 |
| WO | WO 2008/083290 | 7/2008 |
| WO | WO 2008/127659 | 10/2008 |
| WO | WO 2009/067453 | 5/2009 |
| WO | WO 2009/067543 | 5/2009 |
| WO | WO 2009/108755 | 9/2009 |
| WO | WO 2009/137378 | 11/2009 |
| WO | WO 2009/137649 | 11/2009 |
| WO | WO 2009/155659 | 12/2009 |
| WO | WO 2010/011700 | 1/2010 |
| WO | WO 2010/014819 | 2/2010 |

OTHER PUBLICATIONS

Ueda et al., *J. Antibiot.* (Tokyo) 47:301-310, 1994.

"Novel Anticancer Drug-FK 228-From Discovery to Mechanism of Action," presentation at the 4th ISCC Feb. 12, 1999.

Bates et al., "A Phase I Study of FR901228 (Depsipeptide), a Histone Deacetylase Inhibitor," *Clinical Pharmacology*, American Society of Clinical Oncology, Abstract 693 (1999).

Bird et al., "Helper T Cell Differentiation Is Controlled by the Cell Cycle," *Immunity* 9:229-237 (1998).

Byrd et al., "Depsipeptide (FR901228): A Novel Therapeutic Agent With Selective, In Vitro Activity Against Human B-Cell Chronic Lymphocytic Leukemia Cells," *Blood* 94(4):1401-1408 (1999).

Cancer Therapy Evaluation Program, 1998, Clinical Center NIH, Ohio State University.

Dai et al., "Interactions between bortezomib and romidepsin and belinostat in chronic lymphocytic leukemia cells," *Clinical Cancer Research* 14(2):549-558 (2008).

Dail et al., "The HDAC inhibitors romidepsin and PXD101 interact synergistically with Bortezomib in human chronic lymphocytic leukemia (CLL) cells in association with NF-kappa B inactivation," *Proceedings of the American Association for Cancer Research* 48:437-438 (2007).

Furumai et al., "FK228 (Depsipeptide) as a Natural Prodrug That Inhibits Class I Histone Deacetylases," *Cancer Research*, Sep. 1, 2002, 4916-4921.

Glaser et al., "HDAC inhibitors: Clinical update and mechanism-based potential," *Biochemical Pharmacology* 74(5):659-671 (2007).

International Search Report, PCT/US2007/089067, date of mailing Aug. 20, 2008.

International Search Report, PCT/US2008/000850, date of mailing Jun. 26, 2008.

Lundqvist et al., "Bortezomib and depsipeptide sensitize tumors to tumor necrosis factor-related apoptosis-inducing ligand: a novel method to potentiate natural killer cell tumor cytotoxicity," *Cancer Research* 66(14):7317-7325 (2006).

Masuoka et al., "Histone deacetylase inhibitors from microorganisms: the Astellas experience," Progress in Drug Research 66:336-359 (2008).

Medical Record for a patient with peripheral T-cell lymphoma, Jan. 12, 1999.

Programme of the 4th Japanese Foundation for Cancer Research, International Symposium on Cancer Therapy (ISCC), Feb. 12, 1999.

Sutheesophon et al., "Histone deacetylase inhibitor depsipeptide (FK228) induces apoptosis in leukemic cells by facilitating mitochondrial translocation of Bax, which is enhanced by the proteasome inhibitor bortezomib," *Acta Haematologica* 115(1-2):78-90 (2006).

Ueda et al., "FR901228, a Novel Antitumor Bicyclic Depsipeptide Produced by *Chromobacterium violaceum* No. 968," *The Journal of Antibiotics* 47(3):315-323 (1994).

Wang et al., "Fungal metabolite FR901228 inhibits c-Myc and Fas ligand expression," *Oncogene* 17:1503-1508 (1998).

(56) References Cited

OTHER PUBLICATIONS

Written Opinion, PCT/US2007/089067, date of mailing Aug. 20, 2008.
Written Opinion, PCT/US2008/000850, date of mailing Jun. 26, 2008.
Xiao et al., "Efflux of Depsipeptide FK228 (FR901228, NSC-630176) Is Mediated by P-Glycoprotein and Multidrug Resistance-Associated Protein 1," *J. Pharm. & Exp. Therapeutics*, V. 313, No. 1, 2005, 268-276.
Xiao et al., "Identification of thiols and glutathione conjugates of depsipeptide FK228 (FR901228), a novel histone protein deacetylase inhibitor, in the blood," *Rapid Commun. Mass Spectrom.* 2003; 17: 757-766.
Yu et al., "The proteasome inhibitor bortezomib interacts synergistically with histone deacetylase inhibitors to induce apoptosis in Bcr/Abl+ cells sensitive and resistant to STI571," *Blood* 102(10):3765-3774 (2003).
Aron et al., *Blood* 102(2):652-658, 2003.
Bates et al., *ASH Annual Meeting Abstracts* 112 (11):1568, 2008.
Bishton et al., *Expert Rev Anticancer Ther* 7(10):1439-1449, 2007.
Bhalla, *J Clin Oncol* 23(17):3971-3993, 2005.
Bogden et al., *Exp Cell Biol* 47:281-293. 1979.
Bolden et al., *Nat Rev Drug Discovery* 5(9):769-784, 2006.
Budillon et al., *Eur J Cancer* 38:S29, 2002 (XP-004403521).
Butler et al., *Cancer Res* 60:5165-5170, 2000.
Byrd et al., *Blood* 105(3):959-967, 2005.
Catley et al., *Blood* 108(10):3441-3449, 2006.
Chan et al., *Invest New Drugs* 15(3):195-206, 1997.
Cheson et al., *Review Clin Exp Hematol* 4(2):134-166, 2000.
Conway et al., *Eur J Cancer* 34(11):1741-1748, 1998 (XP-004285125).
Database Biosis 'Online, AN-PREV200400024248, XP-002342749, "Anti-Tumor Efficacy of Four Different Histone Deacetylase Inhibitors on Hepatoma Cells in Vitro", 2003 (Abstract No. T1786).
Dokmanovic & Marks, *J Cell Biochem* 96(2):293-304, 2005.
Fiebig et al., *Cancer* 6:213, 2006.
Garcia-Manero et al., *Blood* 108(10):3271-3279, 2006.
Geldof et al., *Cancer Chemother & Pharmacol* 44(4):312-318, 1999.
Gore et al., *Clin Cancer Res* 7(8):2330-2339, 2001.
Gore et al., *Cancer Res* 66(12):6361-6369, 2006.
Han et al., *Cancer Res* 60(21):6068-6074, 2000.
Harrison et al., *ASH Annual Meeting Abstracts* 112(11):3698, 2008.
Inoue et al., Gan to Kagaku Ryoho 14(5Pt2):1629-1635, 1987 (Abstract).
Jones & Baylin, *Nat Rev Genet* 3(6):415-428, 2002.
Jones & Baylin, *Cell* 128:683-692, 2007.
Jung et al., *J Med Chem* US 42(22):4669-4679, 1999.
Kano et al., *Japanese J Clin Hematology* 43(8):116, 2002.
Khan et al., *Br J Haematol* 125(2):156-161, 2004.
Kim et al., *ASH Annual Meeting Abstracts* 112(11):263, 2008.
Kitazono et al., *J Clin Endocrin* 86(7):3430-3435, 2001.
Kitazono et al., *Cancer Res* 61:6328-6330, 2001.
Kitazono et al., *Int J Cancer* 99:453-459, 2002.
Kitazono et al., *Proc Amer Assoc Cancer Res Annual* 43:799, 2002 (Abstract only).
Klimek et al., *Clin Cancer Res* 14(3):826-832, 2008.
Klisovic et al., *Invest Ophthalmol Vis Sci* 44(6):2390-2398, 2003.
Komatsu et al., *Cancer Res* 61(11):4459-4466, 2001.
Kosugi et al., *Japanese J Cancer Res* 92(5):529-536, 2001.
Kuendgen et al., *Blood* 104(5):1266-1269, 2004.
Li et al., *J Am Chem Soc* 118(30):7237-7238, 1996.
Maeda et al., *Blood* 96(12):3847-3856, 2000.
Magner et al., *J Immunol* 165(12):7017-7024, 2000.
Marks et al., *J Natl Cancer Inst* 92(15):1210-1216, 2000.
Marshall et al., *J Exp Ther Oncol* 2(6):325-332, 2002.
Mertins et al., *Proc Amer Assoc Cancer Res Annual Meetings* 40:623, 1999.
Mitsiades et al., *Proc Natl Acad Sci USA* 101(2):540-545, 2004.
Molife et al., *J Clin Oncol* (Meeting Abstracts) 24(18 Suppl):14554, 2006.
Murata et al., *Japanese J Cancer Res* 91:1154-1160, 2000.
Nebbioso et al., *Nat Med* 11(1):77-84, 2005.
Nebozhyn et al., *Blood* 107(8):3189-3196, 2006.
Newbold et al., *Mol Cancer Ther* 7(5):1066-1079, 2008.
Niesvizky et al., *ASH Annual Meeting Abstracts* 106(11):2574, 2005.
Nishimura et al., *J Antibiot* XLII(4):553-557, 1989.
Nuijen et al., *Medline*, 2001, XP-002206588.
Odenike et al., *Clin Cancer Res* 14(21):7095-7101, 2008.
Paoluzzi et al., *Clin Cancer Res* 16(2):554-565, 2010.
Peart et al., *Cancer Res* 63(15):4460-4471, 2003.
Peart et al., *Proc Natl Acad Sci USA* 102(10):3697-3702, 2005.
Pei et al., *Clin Cancer Res* 10(11):3839-3852, 2004.
Piekarz et al., *Blood* 98(9):2865-2868, 2001.
Piekarz et al., *Blood* 103(12):4636-4643, 2004.
Piekarz et al., *ASH Annual Meeting Abstracts* 106(11):231, 2005.
Piekarz et al., *Clin Cancer Res* 12(12):3762-3763, 2006.
Piekarz et al., *J Clin Oncol* (Meeting Abstracts) 25(18 Suppl):8027, 2007.
Piekarz et al., *ASH Annual Meeting Abstracts* 112(11):1567, 2008.
Piekarz et al., *Clin Cancer Res* 15(12):3918-3926, 2009.
Piekarz et al., *J Clin Oncol* 27(32):5410-5417, 2009.
Prince et al., *Clin Cancer Res* 15(12):3958-3969, 2009.
Rasheed et al., *Expert Opin Investig Drugs* 16(5):659-678, 2007.
Richon et al., *Proc Natl Acad Sci USA* 97(18):10014-10019, 2000.
Richon et al., *Clin Cancer Res* 8(3):662-664, 2002.
Robey et al., *Clin Cancer Res* 12(5):154701555, 2006.
Roychowdhury et al., *J Natl Cancer Inst* 96(19):1447-1457, 2004.
Sakai et al., *J Biol Chem* 277(50):48714-48723, 2002.
Sandor et al., *Br J Cancer* 83(6):817-825, 2000.
Sandor et al., *Clin Cancer Res* 8(3):718-728, 2002.
Sasakawa et al., *Biochem Pharmacol* 64(7):1079-1090, 2002.
Sawa et al., *Proc of Japanese Cancer Assoc* 60:597, 2001 (w/English translation).
Sawa et al., *Acta Neuropathol* (Berlin) 107(6):523-531, 2004.
Schrump et al., *Clin Cancer Res* 14(1):188-198, 2008.
Schwartsmann et al., *The Lancet Oncology* 2(4):221-225, 2001.
Sreedharan et al., *Proc Amer Assoc Cancer Res* 44(2 ed.):742, 2003 (XP-001154773).
Stadler et al., *Clin Genitourin Cancer* 5(1):57-60, 2006.
Su et al., *J Clin Oncol* (Meeting Abstracts) 24(18 Suppl):5554, 2006.
Testa Bernard, *Chemistry & Biodiversity* 4(9):2031-2122, 2007.
Ueda et al., *Biosci Biotechnol Biochem* 58(9):1579-1583, 1994.
Vrana et al., *Oncogene* 18(50):7016-7025, 1999.
Watanabe et al., *Int J Cancer* 124(1):55-67, 2009.
Weidle et al. *Anticancer Res* 20:1471-1486, 2000.
Whitehead et al., *J Clin Oncol* (Meeting Abstracts) 24(18 Suppl):3598, 2006.
Whittaker et al., *J Clin Oncol* (Meeting Abstracts) 24(18 Suppl):3063, 2006.

\* cited by examiner

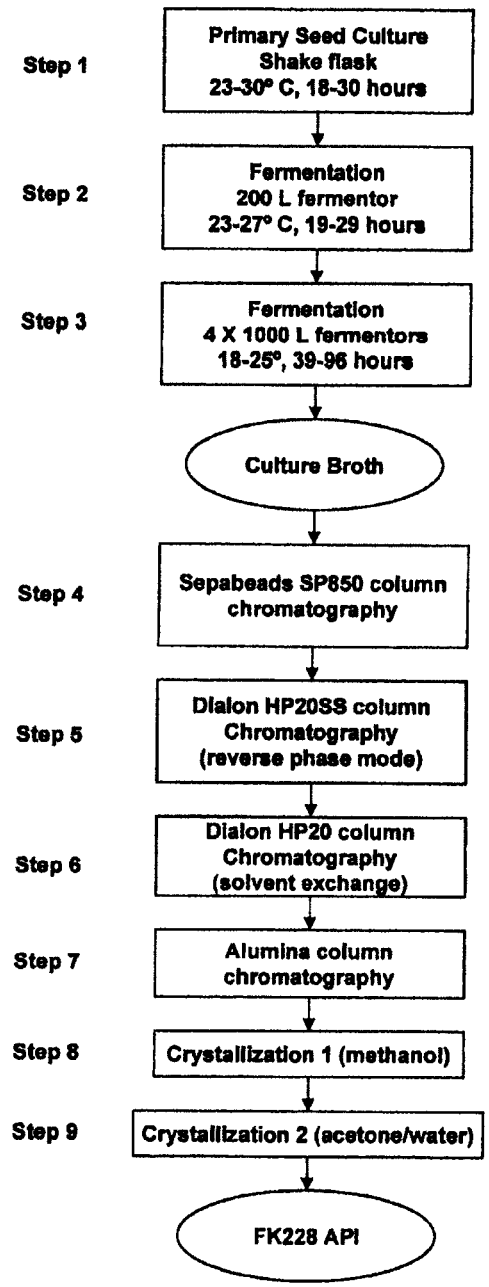

PREPARATION OF ROMIDEPSIN

RELATED APPLICATIONS

The present application claims priority under 35 U.S.C. §119(e) to U.S. provisional patent applications, U.S. Ser. No. 60/882,698, and U.S. Ser. No. 60/882,704, both of which were filed Dec. 29, 2006, each of which is incorporated herein by reference.

BACKGROUND OF THE INVENTION

Romidepsin is a natural product which was isolated from *Chromobacterium violaceum* by Fujisawa Pharmaceuticals. See Published Japanese Patent Application Hei 7 (1995)-64872; U.S. Pat. No. 4,977,138, issued Dec. 11, 1990, each of which is incorporated herein by reference. It is a bicyclic peptide consisting of four amino acid residues (D-valine, D-cysteine, dehydrobutyrine, and L-valine) and a novel acid (3-hydroxy-7-mercapto-4-heptenoic acid). Romidepsin is a depsipeptide which contains both amide and ester bonds. In addition to the production of *C. violaceum* using fermentation, romidepsin can also be prepared by synthetic or semi-synthetic means. The total synthesis of romidepsin reported by Kahn et al. involves 14 steps and yields romidepsin in 18% overall yield. *J. Am. Chem. Soc.* 118:7237-7238, 1996. The structure of romidepsin is shown below:

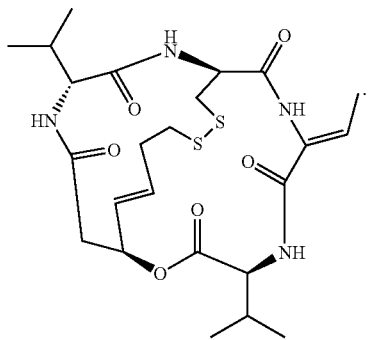 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

Romidepsin has been shown to have anti-microbial, immunosuppressive, and anti-tumor activities. Romidepsin is currently being tested, for example, for use in treating patients with hematological malignancies (e.g., cutaneous T-cell lymphoma (CTCL), peripheral T-cell lymphoma (PTCL), multiple myeloma, etc.) and solid tumors (e.g., prostate cancer, pancreatic cancer, etc.). It is thought to act by selectively inhibiting deacetylases (e.g., histone deacetylase, tubulin deacetylase), promising new targets for the development of a new class of anti-cancer therapies. Nakajima et al., *Experimental Cell Res.* 241:126-133, 1998. One mode of action involves the inhibition of one or more classes of histone deacetylases (HDAC).

Histone deacetylase is a metallodeacetylation enzyme having zinc in its active site. Finnin et al., *Nature*, 401:188-193, 1999. This enzyme is thought to regulate the expression of certain genes by modulating the affinity of acetylated histones for DNA. The acetylation of histones is controlled by the balance between acetylation and deacetylation. The acetylation of histones occurs at a lysine residue of the histone protein. Acetylation of the lysine residue causes the protein to lose some of its positive charge, thereby decreasing its interaction with DNA. Romidepsin has been found to cause the increased acetylation of histones and other regulatory proteins in treated cells. This affects the transcriptional control of various genes involved in cell cycle control, differentiation, and apoptosis. More recently, HDAC inhibitors have been implicated in the control of autophagy.

In addition to romidepsin, various derivatives have been prepared and studied. The following patent and patent applications describe various derivatives of romidepsin: U.S. Pat. No. 6,548,479; WO 05/0209134; WO 05/058298; and WO 06/129105; each of which is incorporated herein by reference.

Given the interest in romidepsin as a pharmaceutical agent, there remains a need for preparing large quantities of highly purified material in a cost effective manner. Various reports of purifying romidepsin from fermentation broth have been reported. U.S. Pat. No. 4,977,138; International PCT Application WO 02/20817; each of which is incorporated herein by reference. For example, WO 02/20817 describes increasing the yield of romidepsin from a fermentation process by the addition of specific amino acids such as L-cysteine to the culture medium. Although such discoveries have provided for improved yields of romidepsin by fermentation, there remains a need for better ways of preparing large quantities of pure romidepsin for research and medicinal use.

SUMMARY OF THE INVENTION

The present invention is based on the recognition that the published procedures for isolating romidepsin do not reproducibly yield pure romidepsin, in particular, romidepsin free of contaminants such as dimerized, oligomerized, or polymerized romidepsin. Based on this recognition, the present invention provides a system for reproducibly preparing romidepsin under conditions that reduce the levels of these contaminating side products. Producing, purifying, and/or storing romidepsin at an apparent pH less than approximately 6.5, more preferably less than approximately 6.0, has been found to prevent the formation of dimerized, oligomerized, or polymerized romidepsin. This improvement in the purification process of romidepsin allows for higher yields of romidepsin and/or higher purity romidepsin than that provided by known processes. Such an improvement is particularly useful for preparing pharmaceutical grade romidepsin for use in humans.

Romidepsin is typically produced by purifying it from a culture of a microorganism (e.g., *Chromobacterium violaceum*) that produces the natural product. The present invention demonstrates that it is necessary to maintain a low apparent pH during at least some of the purification steps in order to eliminate or reduce the formation of reduced romidepsin which can subsequently dimerize, oligomerize, or polymerize to form undesired contaminants.

One or more of the purification steps are performed at an apparent pH less than 6.5, or even an apparent pH less than 6.0. In certain embodiments, one or more purification steps are performed at an apparent pH ranging from 4.0 to 6.0. In certain embodiments, all of the purification steps are carried out at an apparent pH ranging from approximately 4.0 to approximately 6.0. In order to prevent the formation of undesired contaminants, the apparent pH of a solution containing romidepsin is not allowed to reach an apparent pH above approximately 7.0, or more preferably above approximately 6.0. The apparent pH of all purification processes is preferably monitored and subsequently adjusted, if need be, to an apparent pH below approximately 6.0. In certain embodiments, it is maintained within the apparent pH range of approximately 4.0 to approximately 6.0. The control of apparent pH in purification steps towards the end of the process or steps using aqueous solutions have been found to be particularly useful in diminishing or eliminating the formation of undesired contaminants. Any acid or buffer may be used to control pH. In certain embodiments, an organic acid such as acetic acid or formic acid is used to control pH in one of more of the purification steps. In certain embodiments, an inorganic acid such as phosphoric acid or hydrochloric acid is used.

Any procedure for purifying romidepsin, whether from fermentation, semi-synthesis, or total synthesis, can be modified based on the present invention to prevent the formation of undesired side products by monitoring apparent pH and reducing the apparent pH if necessary.

In one aspect, the invention provides a process for preparing romidepsin from a culture of *Chromobacterium violaceum*. The fermentation broth is acidified in order to inactivate or kill the microorganisms in the culture. The acidified fermentation broth is preliminarily purified by batch or column chromatography. Subsequently, multiple column chromatography steps may be used to achieve the desired level of purity. In certain embodiments, the first chromatography utilizes SEPABEADS SP850, a non-ionic adsorption resin. The romidepsin may be further purified by additional column chromatography steps. In certain embodiments, the romidepsin is subsequently purified by column chromatography using DIAION HP20SS resin, followed by column chromatography using DIAION HP20 resin, and finally by column chromatography on alumina. In certain embodiments, the column chromatography is performed at an apparent pH ranging from approximately 4 to approximately 6. In certain particular embodiments, the second column chromatography step is performed at a reduced apparent pH (e.g., apparent pH of approximately 4 to 6). The romidepsin is optionally further purified by crystallization. One or more crystallization steps may be performed. In certain embodiments, the romidepsin is first crystallized using methanol and then crystallized using 85% aqueous acetone. The resulting romidepsin is then optionally filtered, washed, and dried. In certain embodiments, the crystallization steps or any subsequent steps are performed at a reduced apparent pH ranging from approximately 4.0 to approximately 6.0. It is particularly important that the final steps be performed at a reduced apparent pH since no subsequent purification steps are available for removing undesired contaminants. Any equipment (e.g., tubing, pumps, filters, dryers, etc.) used in the fermentation and/or purification processes is washed with water or an acidic solution (e.g., acetic acid) to remove or neutralize any alkaline residue on the equipment.

Furthermore, preparation of pharmaceutical dosage forms of romidepsin, including compounding with excipients, solvents, co-solvents, and/or other agents used to enhance the pharmacological activity of romidepsin, may be performed at a reduced apparent pH (e.g., an apparent pH less than approximately 4.0) in order to minimize formation of dimerized, oligomerized, or polymerized romidepsin.

In another aspect, the invention provides a compositions of romidepsin substantially free of contaminating dimerized, oligomerized, or polymerized romidepsin. The romidepsin provided by the present invention is greater than 98% monomeric, greater than 99% monomeric, greater than 99.95% monomeric, or greater than 99.9% monomeric. In some embodiments, the romidepsin is preferably greater than 98% pure, greater than 99% pure, greater than 99.95% pure, or greater than 99.9% pure with respect to all contaminants. In certain embodiments, the romidepsin includes less than 1.0%, less than 0.5%, less than 0.2%, or less than 0.1% of total other unknowns. The composition of romidepsin preferably includes no detectable dimerized, oligomerized, or polymerized material. The purity of the romidepsin is typically determined by high performance liquid chromatography (HPLC), infrared spectroscopy, powder x-ray diffraction (XRPD) analysis, gas chromatography (GC), specific rotation, or NMR spectroscopy. In certain embodiments, the purity is determined by measuring the specific rotation of a solution of romidepsin in chloroform. The invention also provides buffered preparations of romidepsin that maintain the apparent pH of the preparation below approximately 6.0, preferably, between approximately 4.0 and approximately 6.0. Such preparations typically have an extended shelf-life.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (D)-isomers, (L)-isomers, (–)- and (+)-isomers, racemic mixtures thereof, and other mixtures thereof, as falling within the scope of the invention. Additional asymmetric carbon atoms may be present in a substituent such as an aliphatic (e.g., alkyl) or heteroaliphatic group. All such isomers, as well as mixtures thereof, are considered to be within this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. In certain embodiments, only one hydrogen radical in a given structure is replaced with the radical of a specified substituent. In other embodiments, one, two, or three hydrogen radicals in a given structure are replaced with the same or different radicals of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of proliferative diseases such as cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$;

—CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

"Independently selected": The term "independently selected" is used herein to indicate that the R groups can be identical or different.

Definitions of other terms used throughout the specification include:

"Acid": The term "acid", as used herein, refers to inorganic and organic acids. Examples of inorganic acids include, but are not limited to, hydrochloric acid, hydrobromic acid, hydroiodic acid, nitric acid, sulfuric acid, and phosphoric acid. Examples of organic acids include, but are not limited to, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Any acid may be used to adjust the pH of the buffers or solutions of romidepsin or those used in the purification of romidepsin. In certain embodiments, acetic acid is used. In certain embodiments, hydrochloric acid is used. In certain embodiments, citric acid is used. In certain embodiments, sulfuric acid is used.

"Depsipeptide": The term "depsipeptide", as used herein, refers to polypeptides that contain both ester and amide bonds. Naturally occurring depsipeptides are usual cyclic. Some depsipeptides have been shown to have potent antibiotic activity. Examples of depsipeptides include actinomycin, enniatins, valinomycin, and romidepsin.

"Peptide" or "protein": According to the present invention, a "peptide" or "protein" comprises a string of at least three amino acids linked together by peptide bonds. The terms "protein" and "peptide" may be used interchangeably. Peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, peptide refers to depsipeptide.

"Romidepsin": The term "romidepsin", refers to a natural product of the chemical structure:

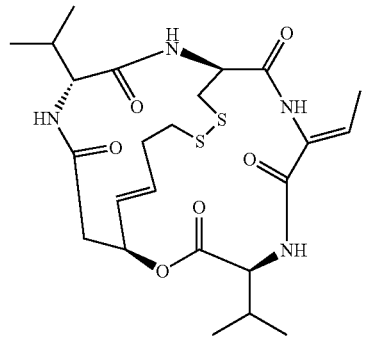

Romidepsin is a potent HDAC inhibitor and is also known in the art by the names FK228, FR901228, NSC630176, or depsipeptide. The identification and preparation of romidepsin is described in U.S. Pat. No. 4,977,138, which is incorporated herein by reference. The molecular formula is $C_{24}H_{36}N_4O_6S_2$; and the molecular weight is 540.71. Romidepsin has the chemical name, (1S,4S,10S,16E,21R)-7-[(2Z)-ethylidene]-4,21-diisopropyl-2-oxa-12,13-dithia-5,8,20,23-tetraazabicyclo[8.7.6]tricos-16-ene-3,6,9,19,22-pentanone. Romidepsin has been assigned the CAS number 128517-07-7. In crystalline form, romidepsin is typically a white to pale yellowish white crystal or crystalline powder. The term "romidepsin" encompasses this compound and any pharmaceutically acceptable salt forms thereof. In certain embodiments, the term "romidepsin" may also include prodrugs, esters, protected forms, and derivatives thereof.

BRIEF DESCRIPTION OF THE DRAWING

FIG. 1 shows a flowchart for purifying romidepsin from a culture of Chromobacterium violaceum.

DETAILED DESCRIPTION OF CERTAIN EMBODIMENTS OF THE INVENTION

The present invention provides an improved system for preparing romidepsin, a known histone deacetylase (HDAC) inhibitor useful in the treatment of cancer. Unfortunately, published methods for preparing romidepsin do not reproducibly yield pure, monomeric romidepsin. Surprisingly, pH control during the purification process has been found to provide pure, monomeric romidepsin reproducibly. In particular, performing at least certain parts of the purification process at reduced apparent pH (e.g., an apparent pH ranging from 4 to 6) results in higher yields of purified, monomeric romidepsin without contaminating dimerized, oligomerized, or polymerized side products.

Romidepsin is a cyclic depsipeptide having a disulfide bond. The present invention is based on the discovery that exposure of romidepsin to basic conditions (e.g., greater than an apparent pH of ~7) facilitates the reduction of this disulfide bond. Reduced romidepsin with its free thiols has been found to be susceptible to dimerization, oligomerization, or polymerization. Such adducts are typically insoluble and difficult to remove from purified romidepsin. In certain embodiments, such contaminating adducts prevent a preparation of romidepsin from meeting the desired specifications (e.g., solubility, degree of purity, optical rotation, etc.). In pharmaceutical compositions, these adducts decrease the purity of the active agent, romidepsin. Since romidepsin is being used as a pharmaceutical agent in humans, it is important that pure, stable, monomeric romidepsin be reproducibly obtained from a fermentation of *Chromobacterium violaceum*. The present invention stems from the recognition that alkaline conditions cause the formation of these undesired romidepsin adducts and provides a novel solution to this problem.

The inventive system is also useful in preparing derivatives of romidepsin, particularly derivatives containing a disulfide bond. In certain embodiments, the derivative of romidepsin is of formula (I):

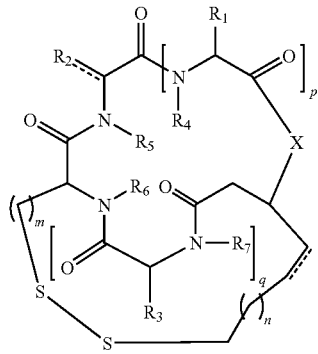

(I)

wherein
m is 1, 2, 3 or 4;
n is 0, 1, 2 or 3;
p and q are independently 1 or 2;
X is O, NH, or $NR_8$;
$R_1$, $R_2$, and $R_3$ are independently hydrogen; unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl;
$R_4$, $R_5$, $R_6$, $R_7$ and $R_8$ are independently hydrogen; or substituted or unsubstituted, branched or unbranched, cyclic or acyclic aliphatic; and pharmaceutically acceptable salts thereof. In certain embodiments, m is 1. In certain embodiments, n is 1. In certain embodiments, p is 1. In certain embodiments, q is 1. In certain embodiments, X is O. In certain embodiments, $R_1$, $R_2$, and $R_3$ are unsubstituted, or substituted, branched or unbranched, acyclic aliphatic. In certain embodiments, $R_4$, $R_5$, $R_6$, and $R_7$ are all hydrogen.

In certain embodiments, the derivative of romidepsin is of formula (II):

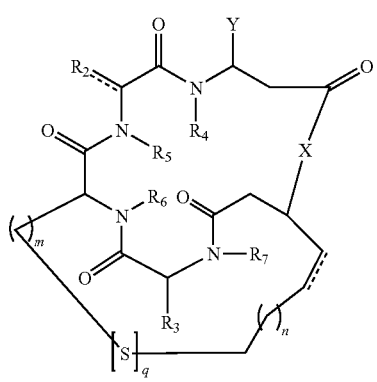

(II)

wherein:
m is 1, 2, 3 or 4;
n is 0, 1, 2 or 3;
q is 2 or 3;
X is O, NH, or $NR_8$;
Y is $OR_8$, or $SR_8$;
$R_2$ and $R_3$ are independently hydrogen; unsubstituted or substituted, branched or unbranched, cyclic or acyclic aliphatic; unsubstituted or substituted, branched or unbranched, cyclic or acylic heteroaliphatic; unsubstituted or substituted aryl; or unsubstituted or substituted heteroaryl;
$R_4$, $R_5$, $R_6$, $R_7$ and $R_8$ are independently selected from hydrogen; or substituted or unsubstituted, branched or unbranched, cyclic or acyclic aliphatic; and pharmaceutically acceptable salts thereof. In certain embodiments, m is 1. In certain embodiments, n is 1. In certain embodiments, q is 2. In certain embodiments, X is O. In other embodiments, X is NH. In certain embodiments, $R_2$ and $R_3$ are unsubstituted or substituted, branched or unbranched, acyclic aliphatic. In certain embodiments, $R_4$, $R_5$, $R_6$, and $R_7$ are all hydrogen.

In certain embodiments, the derivative of romidepsin is of formula (III):

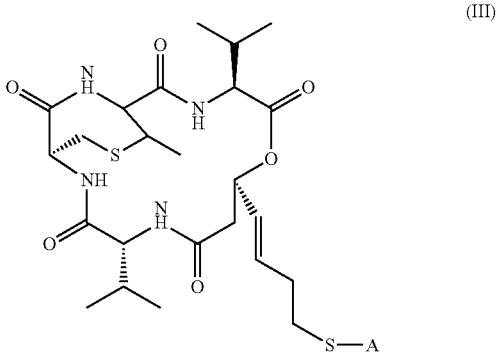

(III)

wherein A is a moiety that is cleaved under physiological conditions to yield a thiol group and includes, for example, an aliphatic or aromatic acyl moiety (to form a thioester bond); an aliphatic or aromatic thioxy (to form a disulfide bond); or the like; and racemates, enantiomers, isomers, tautomers, salts, esters, and prodrugs thereof. Such aliphatic or aromatic groups can include a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. A can be, for example, —$COR_1$, —SC(=O)—O—$R_1$, or —$SR_2$. $R_1$ is independently hydrogen; substituted or unsubstituted amino; substituted or unsubstituted, branched or unbranched, cyclic or acyclic aliphatic; substituted or unsubstituted aromatic group; substituted or unsubstituted heteroaromatic group; or a substituted or unsubstituted heterocyclic group. In certain embodiment, $R_1$ is hydrogen, methyl, ethyl, n-propyl, iso-propyl, n-butyl, isobutyl, benzyl, or bromobenzyl. $R_2$ is a substituted or unsubstituted, branched or unbranched, cyclic or acyclic aliphatic group; a substituted or unsubstituted aromatic group; a substituted or unsubstituted heteroaromatic group; or a substituted or unsubstituted heterocyclic group. In certain embodiments, $R_2$ is methyl, ethyl, 2-hydroxyethyl, isobutyl, fatty acids, a substituted or unsubstituted benzyl, a substituted or unsubstituted aryl, cysteine, homocysteine, or glutathione.

In certain embodiments, the derivative of romidepsin is of formula (IV) or (IV'):

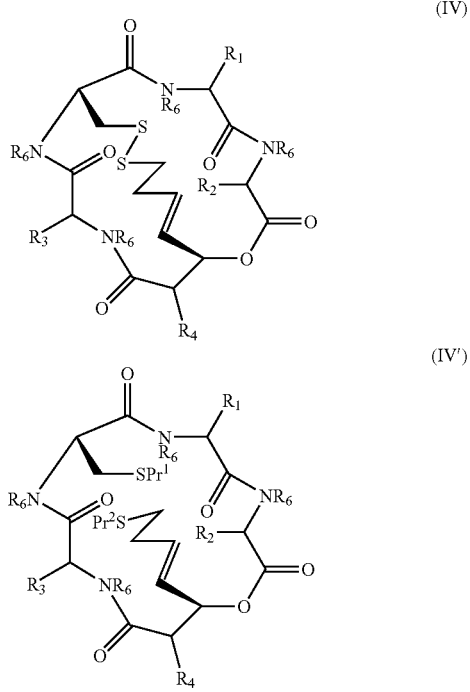

wherein $R_1$, $R_2$, $R_3$, and $R_4$ are the same or different and represent an amino acid side chain moiety, each $R_6$ is the same or different and represents hydrogen or $C_1$-$C_4$ alkyl, and $Pr^1$ and $Pr^2$ are the same or different and represent hydrogen or thiol-protecting group. In certain embodiments, the amino acid side chain moieties are those derived from natural amino acids. In other embodiments, the amino acid side chain moieties are those derived from unnatural amino acids. In certain embodiments, each amino acid side chain is a moiety selected from —H, —$C_1$-$C_6$ alkyl, —$C_2$-$C_6$ alkenyl, -L-O—C(O)—R', -L-C(O)—O—R", -L-A, -L-NR"R", -L-Het-C(O)—Het-R", and -L-Het-R", wherein L is a $C_1$-$C_6$ alkylene group, A is phenyl or a 5- or 6-membered heteroaryl group, each R' is the same or different and represents $C_1$-$C_4$ alkyl, each R" is the same or different and represent H or $C_1$-$C_6$ alkyl, each -Het- is the same or different and is a heteroatom spacer selected from —O—, —N(R''')—, and —S—, and each R''' is the same of different and represents H or $C_1$-$C_4$ alkyl. In certain embodiments, $R_6$ is —H. In certain embodiments, $Pr^1$ and $Pr^2$ are the same or different and are selected from hydrogen and a protecting group selected from a benzyl group which is optionally substituted by $C_1$-$C_6$ alkoxy, $C_1$-$C_6$ acyloxy, hydroxy, nitro, picolyl, picolyl-N-oxide, anthrylmethyl, diphenylmethyl, phenyl, t-butyl, adamanthyl, $C_1$-$C_6$ acyloxymethyl, $C_1$-$C_6$ alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and $C_1$-$C_6$ alkylcarbamoyl. In certain embodiments, $Pr^1$ and $Pr^2$ are hydrogen. Various romidepsin derivatives of formula (IV) and (IV') are disclosed in published PCT application WO 2006/129105, published Dec. 7, 2006; which is incorporated herein by reference.

The present invention is also useful in the preparation of other natural products containing a disulfide linkage. The inventive may be used in the preparation of cyclic or non-cyclic peptides. In certain embodiments, cyclic peptides containing a disulfide bond are purified using the inventive system. In certain embodiments, other depsipeptides besides romidepsin are purified based on the present invention of using a reduced apparent pH to limit or eliminate the reduction of an intramolecular disulfide bond.

According to the invention, the formation of undesired adducts of romidepsin or a derivative of romidepsin can be prevented by not allowing romidepsin to be prepared or purified under conditions greater than an apparent pH of ~7.0, more preferably greater than an apparent pH of ~6.5, or most preferably greater than an apparent pH of ~6.0. The preparation and purification is typically kept between approximately apparent pH 4.0 and apparent pH 6.0. In certain embodiments, an even lower apparent pH may be used. This recognition can be applied to any production or purification method for preparing romidepsin. In certain embodiments, the romidepsin is purified from a fermentation. In other embodiments, romidepsin is prepared by semi-synthesis or total synthesis. This discovery may also be applied to the preparation and/or production of analogs or derivatives of romidepsin (e.g., salts, esters, pro-drugs, isomers, enantiomers, tautomers, protected forms, derivatized products, etc.). Certain derivatives of romidepsin are described herein.

Processes for preparing romidepsin are known in the art. See, e.g., Ueda et al., *J. Antibiot.* (Tokyo) 47:301-310, 1994; Nakajima et al., *Exp. Cell Res.* 241:126-133, 1998; WO 02/20817; U.S. Pat. No. 4,977,138; each of which is incorporated herein by reference. Since romidepsin is a natural product, it is typically prepared by isolating it from a fermentation of a microorganism that produces it. In certain embodiments, the microorganism belongs to the genus *Chromobacterium*. An exemplary microorganism that is known to produce romidepsin is *Chromobacterium violaceum*. Any natural or man-made variant of *Chromobacterium violaceum* may be used to isolate romidepsin using the inventive system. In certain embodiments, the strain of *Chromobacterium violaceum* is *Chromobacterium violaceum* WB968. In certain embodiments, the strain of *Chromobacterium violaceum* is a mutant strain of *Chromobacterium violaceum* WB968. In certain embodiments, the microorganism is genetically engineered to produce romidepsin. For example, the genes responsible for the cellular machinery that produce romidepsin can be placed into another microorganism such as bacteria or fungi.

The organism is grown under conditions suitable for its production of romidepsin. Preferably, the culture conditions are optimized to produce a high level of romidepsin with minimal levels of contaminating adducts or degradants. The medium of the culture preferably includes a nitrogen and carbon source and any essential vitamins and minerals. The culture is typically grown under aerobic conditions. The size of the culture may range from 10 mL to 10,000 L or even larger. In certain embodiments, the culture volume is greater than 500 L. In other embodiments, the volume is greater than 1000 L. In yet other embodiments, the volume is greater than 2000 L. In other embodiments, the volume is greater than 3000 L. In other embodiments, the volume is greater than 5000 L. In other embodiments, the volume is greater than 6000 L. In other embodiments, the volume is greater than 7000 L. In other embodiments, the volume is greater than 8000 L. In other embodiments, the volume is greater than 9000 L. In certain embodiments, the culture volume ranges from approximately 5000 L to approximately 10000 L. Shake flasks, fermenters, bioreactor, or any other apparatus useful in fermenting microorganisms may be used. As appropriate, seed cultures and small fermenter cultures are used to seed progressively larger cultures.

In certain embodiments, an anti-foaming agent (e.g., polyalkylene glycol antifoam (Adekanol LG-109)) is used in larger cultures. Other commercially available anti-foaming agents may also be used. Anti-foaming agents are particularly useful when a fermenter is used for the production of romidepsin.

The carbon source in the culture medium can be any carbohydrate. In certain embodiments, the carbon source is a monosaccharide or disaccharide (e.g., glucose). In certain particular embodiments, the carbon source is glucose or maltodextrin. Other carbohydrates such as starch, maltose, fructose, or glycerin may be used in certain embodiments. In certain embodiments, the nitrogen source is an ammonium salt such as ammonium sulfate, ammonium nitrate, ammonium phosphate, etc. In other embodiments, the nitrogen source is plant peptone (e.g., polypeptone NS, corn steep liquor, Hinute R). Other nitrogen sources that may be used include bouillon, yeast extract, soy peptone, gluten meal, cotton seed flour, soybean meal, dried yeast, and wheat germ. In certain embodiments, the nitrogen source is urea or amino acids. In certain embodiments, the nitrogen source is an organic small molecule containing nitrogen. In certain embodiments, the medium is supplemented with amino acids. For example, the medium may be supplemented with L-arginine, L-histidine, or L-cysteine. In certain embodiments, the medium is supplemented with L-cysteine. See WO 02/20817; incorporated herein by reference. In certain embodiments, the medium is supplemented with L-cysteine and L-valine. Such supplementation is thought to increase the amount of romidepsin produced in the fermentation and/or reduce the amount of related substances and/or degradants. The culture medium may include minerals such as magnesium (e.g., magnesium sulfate), and phosphate (e.g., potassium dihydrogenphosphate, disodium hydrogenphosphate). In certain embodiments, the culture medium includes glucose, plant peptone (polypeptone NS) or corn steep liquor (CSL), magnesium sulfate, and water. In certain embodiments, the culture medium includes glucose, polypeptone (polypeptone NS), magnesium sulfate, an antifoaming agent, and water. In certain embodiments, the culture medium includes glucose (0.45-1.0%), plant peptone (polypeptone NS) or CSL (0.9-4.0%), magnesium sulfate (0.0054-0.010%), an antifoaming agent (0.09%-0.11%), and water (balance). In certain embodiments, the culture medium includes glucose, oxidized starch (e.g., Pinedex #100) or maltodextrin, soy peptone (e.g., Hinute-R), ammonium sulfate, magnesium sulfate, potassium dihydrogenphosphate, disodium hydrogen phosphate, anti-foaming agent (e.g., Adekanol LG-109), L-cysteine, L-valine, and water. In certain embodiments, the culture medium includes glucose (2-10%), oxidized starch (e.g., Pinedex #100) or maltodextrin (1-15%), soy peptone (e.g., Hinute-R) (1-6%), ammonium sulfate (0-0.5%), magnesium sulfate (0-2%), potassium dihydrogenphosphate (0.275-1.65%), disodium hydrogen phosphate (0.18-1.08%), antifoaming agent (e.g., Adekanol LG-109) (0.2-0.66%), L-cysteine (0-30 mM), L-valine (0-15 mM), and water.

The culture is typically grown under conditions (e.g., temperature, pH, oxygen concentration, etc.) suitable for growth of the organism. In certain embodiments, the pH of the culture is monitored and/or adjusted. The pH of the culture may range from a pH of 5.0 to 7.5. Any organism for romidepsin production will have a preferred temperature for growth depending on the conditions under which the culture is grown. In certain embodiments, the culture is grown at a temperature ranging from 15° C. to 37° C., preferably from 23° C. to 32° C. In certain embodiments, the culture is grown at a temperature between 18° C. to 27° C. In certain embodiments, the culture is grown at a temperature of approximately 18° C. In certain embodiments, the culture is grown at a temperature of approximately 19° C. In certain embodiments, the culture is grown at a temperature of approximately 20° C. In certain embodiments, the culture is grown at a temperature of approximately 21° C. In certain embodiments, the culture is grown at a temperature of approximately 22° C. In certain embodiments, the culture is grown at a temperature of approximately 23° C. In certain embodiments, the culture is grown at a temperature of approximately 24° C. In certain embodiments, the culture is grown at a temperature of approximately 25° C. In certain embodiments, the culture is grown at a temperature of approximately 26° C. In certain embodiments, the culture is grown at a temperature of approximately 27° C. In certain embodiments, the culture is grown at a temperature of approximately 28° C. In certain embodiments, the culture is grown at a temperature of approximately 29° C. In certain embodiments, the culture is grown at a temperature of approximately 30° C. In certain embodiments, the culture is grown at a temperature of approximately 31° C. In certain embodiments, the culture is grown at a temperature of approximately 32° C.

The oxygen concentration in the culture is maintained at a level ranging from 10-50%. In certain embodiments, the oxygen concentration is maintained above 20%. The oxygen level is maintained by aeration, pressure, and/or agitation.

The resulting culture is typically grown for approximately 10-100 hours. The culture may be harvested after 20, 30, 40, 50, 60, 70, or 80 hours. In certain embodiments, the culture is harvested after approximately 30, 35, 40, 45, or 50 hours. In certain embodiments, the culture is harvested at approximately 36 hours. In certain embodiments, the culture is harvested at approximately 50 hours. Typically, the culture is grown until saturation. Since romidepsin is a secondary metabolite, maximal yields are derived from later stage cultures. In some embodiments, the culture is harvested in log phase. As would be appreciated by one of skill in the art, the culture is typically harvested before significant amounts of degradants are formed. The harvest time may be determined empirically by assaying sample of the fermentation for the production of romidepsin. In certain embodiments, the culture is harvested when the titer of romidepsin reaches between 0.5 and 1.5 g/kg. In certain embodiments, the culture is harvested when the titer reaches at least 0.6, 0.7, 0.8, 0.9, 1.0, or 1.1 g/kg. In certain embodiments, the culture is harvested when the titer reaches at least 0.8 g/kg. The sample may also be assayed for related substances or degradants, and the culture harvested when a desired level of romidepsin, desired level of related substances or degradants, or a ratio of the two is achieved. The time of harvesting may also be determined based on the consumption of a component in the media such as glucose. In other embodiments, the time of harvesting is based on the production of a metabolite. The time of harvesting may be determined based on a combination of the above criteria.

After the culture is grown for a sufficient amount of time, the culture is harvested. The desired romidepsin may be found in the culture medium as well as in the cells of the culture. The cells are optionally killed and/or lysed before purification. In certain embodiments, the cells are killed with the addition of acid such as sulfuric acid. In certain embodiments, the pH is lowered to approximately pH 2.0-3.0.

The resulting material is then optionally reduced in volume. The romidepsin is purified by any purification techniques known in the art for purifying peptides, natural products, and/or organic molecules. Exemplary purification techniques include batch chromatography, column chromatography, and crystallization. The purification process may include one or more steps in order to achieve the desired degree of purity. In certain embodiments, the extracted material is purified using a non-ionic adsorption resin. In certain embodiments, a reverse phase resin is used in the fractionation step. In certain particular embodiments, multiple column chromatography steps using a reverse phase resin are used. Exemplary resins useful in the purification process include alumina, silica gel, SEPABEADS SP850, DIAION HP20SS, and DIAION HP20. In certain embodiments, the DIAION HP20SS resin and/or DIAION HP20 resin is obtained from Mitsubishi Chemical Corporation. In certain embodiments, alumina is used as the column material. In certain embodiments, silica gel is used as the resin. In certain embodiments, one or more of the column chromatography steps are performed at an apparent pH less than 6.0. In certain embodiments, one or more of these steps is performed at an apparent pH between 4.0 and 6.0. In certain embodiments, all of the column chromatography steps are performed at an apparent pH less than 6.0. In certain embodiments, all of the column chromatography steps are performed at an apparent pH ranging from 4.0 to 6.0.

In certain embodiments, the purification of romidepsin involves purifying the extracted material using more than one column or batch chromatography steps. In certain embodiments, a batch chromatography step is followed by column chromatography steps. In certain embodiments, the extracted material is purified by batch chromatography with SEPABEADS SP850 resin, followed by a column packed with DIAION HP20SS resin, followed by a column packed with DIAION HP20 resin, and finally followed by a column packed with alumina. All of these chromatography steps are preferably performed at an apparent pH ranging from 4.0 to 6.0. In other embodiments, the extracted material is purified using a column packed with DIAION HP20 resin, followed by a column packed with DIAION HP20SS resin, and finally followed by another column packed with DIAION HP20 resin. In this alternative purification process, all of the column chromatography steps are preferably performed at an apparent pH ranging from 4.0 to 6.0. Each of the columns is optionally washed with water or other aqueous solution followed by elution of romidepsin using an aqueous solution of an organic solvent (e.g., acetone). In certain embodiments, the extracted material is purified using silica gel. Silica gel chromatography may also be used as an additional purification step in conjunction with chromatography using other resins or packing materials. In certain embodiments, the extracted material is purified using alumina. Alumina chromatography may also be used as an additional purification step in conjunction with chromatography using other resins or packing materials.

In certain embodiments, the material with the crude romidepsin is loaded onto a matrix pre-equilibrated at an apparent pH less than 6.0, preferably with an apparent pH ranging from 4.0 to 6.0. The matrix is then washed to remove impurities. Typically, the washing of the matrix is done with a more polar solution (i.e., a higher percentage of water) than the elution of romidepsin. For example, the matrix may be washed with up to 25-50% aqueous acetone followed by elution or romidepsin with 50-100% aqueous acetone. As would be appreciated by one of skill in this art, the washing and elution solvents are determined by the matrix used and the polarity of the compound.

In certain embodiments, one or more of the chromatography steps (including loading, washing, and eluting of the resin) are carried out at an apparent pH less than 6.0. In certain particular embodiments, the chromatography steps are carried out at an apparent pH ranging from 3.0 to 6.0. In certain other embodiments, the chromatography steps are carried out at an apparent pH ranging from 4.0 to 6.0. The apparent pH of the solution loaded onto the matrix may be adjusted to the desired apparent pH with the addition of acid. Any of the acids described herein may be used to lower the apparent pH of the solution. The apparent pH of the wash and eluting solutions may be adjusted to the desired apparent pH as well. In certain embodiments, the apparent pH of all solutions containing romidepsin are kept below an apparent pH of approximately 6.0, thereby preventing the formation of undesired adducts. In certain embodiments, the apparent pH of the solution is buffered at an apparent pH ranging from approximately 4.0 to approximately 6.0. In certain embodiments, the apparent pH of the acetone/water solutions is adjusted to the desired apparent pH using acetic acid, hydrochloric acid, ammonium acetate buffer, or citric acid. In certain embodiments, an acetate buffering system is used.

Romidepsin may alternatively or additionally be purified by crystallization. Purification by crystallization may be used in conjunction with other purification methods including column and/or batch chromatography. In certain embodiments, crystallization is used after purification by column and/or batch chromatography. In certain particular embodiments, the crystallization is performed after purification by column and/or batch chromatography as described above. The crystallization may take place in any suitable solvent. Romidepsin is preferably minimally soluble in the solvent. In certain embodiments, the crystallization solvent is an alcohol. In certain embodiments, the crystallization solvent is methanol. In certain embodiments, the crystallization solvent is ethanol. In certain embodiments, a mixed solvent system is used. The crystallization solvent may be an alcohol/water mixture. In other embodiments, the crystallization solvent is a mixture of acetone and water. In certain particular embodiments, romidepsin is dissolved in an aqueous acetone solution (e.g., 85% acetone) and precipitated by the slow addition of water. In certain embodiments, romidepsin is dissolved in a solvent (e.g., methanol), and the resulting solution is concentrated causing the romidepsin to crystallize out. In other embodiments, the romidepsin is dissolved in a water/organic solvent mixture (e.g., 85% aqueous acetone), and the romidepsin is precipitated by the addition of water. The crystals obtained from a crystallization step are typically collected by filtration and optionally washed and dried. In certain embodiments, the apparent pH of the crystallization solvents is below 6.0. In certain particular embodiments, the apparent pH of the solvent is between 4.0 and 6.0. Any washing of the resulting crystals is also performed at a reduced apparent pH (e.g., between an apparent pH of 4.0 and 6.0).

Alternatively or additionally, the storage or hold time of the romidepsin during the crystallization process is less than about 20 hours. In certain embodiments, the storage or hold time is less than 10 hours. In other embodiments, the storage or hold time is less than 5 hours. In certain particular embodiments, the crystallization process is conducted immediately upon forming the crystallization solution.

The invention provides purified romidepsin free or substantially free of undesired adducts. In certain embodiments, the romidepsin is at least 98% free of contaminating adducts, at least 99% free of contaminating adducts, or at least 99.5% free of adducts. In certain embodiments, the romidepsin is at least 98% monomeric, at least 99% monomeric, or at least 99.5% monomeric. In certain embodiments, the romidepsin is at least 99.9% monomeric. In certain embodiments, the romidepsin is at least 99.95% monomeric. In certain embodiments, the romidepsin includes no detectable dimerized, oligomerized, or polymerized romidepsin.

In certain embodiments, the romidepsin is at least 98% pure, at least 99% pure, or at least 99.5% pure. In certain embodiments, the romidepsin is at least 99.7% pure. In certain embodiments, the romidepsin is at least 99.8% pure. In certain embodiments, the romidepsin is at least 99.9% pure. In certain embodiments, the romidepsin is at least 99.95% pure. In certain particular embodiments, the romidepsin contains less than 0.2% of impurities termed "other unknowns." In certain particular embodiments, the romidepsin contains less than 0.1% of "other unknowns." Such highly purified romidepsin is useful in the preparation of pharmaceutical compositions. Such compositions are particularly useful for the treatment of cancer of other proliferative diseases. The composition may also be used in other diseases that can be treated by inhibiting histone deacetylase activity. The composition may also be used in other diseases that can be treated by inhibiting tubulin deacetylase activity. The composition may also be used in other diseases that can be treated by inhibiting deacetylase activity. The purified romidepsin of the invention is also useful for research purposes.

The purity of the romidepsin can be assessed using any method known in the art. Methods of assessing purity include appearance, HPLC, specific rotation, NMR spectroscopy, IR spectroscopy, UV/Visible spectroscopy, powder x-ray diffraction (XRPD) analysis, elemental analysis, LC-mass spectroscopy, and mass spectroscopy. In certain embodiments, the purity is assessed by HPLC, which has detection limit for impurities of approximately 0.05%. In certain embodiments, the purity is assessed by NMR spectroscopy. In certain embodiments, the purity is assessed by IR spectroscopy. In certain embodiments, the purity is assessed by UV/Visible spectroscopy. In certain embodiments, the purity is assessed by XRPD.

In certain embodiments, the purity is assessed by specific rotation in an appropriate solvent. In certain embodiments, the solvent used for the specific rotation is chloroform ($CHCL_3$). In other embodiments, the solvent used is an alcohol such as methanol or ethanol. In yet other embodiments, the solvent used is water or a water/alcohol solution. In certain embodiments, the specific rotation is checked using a compendial method such as that described in the U.S. Pharmacopeia, European Pharmacopeia, JP Pharmacopeia, or British Pharmacopeia. In certain embodiments, the specific rotation is carried out using a solution of romidepsin in chloroform. The concentration of the solution may range from 5 mg/mL to 30 mg/mL. In certain embodiments, the concentration is approximately 20 mg/mL. The rotation of romidepsin ranges from +380 to +470. In certain embodiments, the specific rotation ranges from +390 to +410. In certain embodiments, the specific rotation ranges from +40.00 to +40.50. In certain particular embodiments, the specific rotation is approximately +400. It has been discovered that the presence of contaminating adducts results in a precipitate when romidepsin is dissolved in chloroform.

When in solution, the romidepsin is preferably stored at an apparent pH below approximately 6.0. In certain embodiments, the apparent pH ranges from approximately 4.0 to approximately 6.0. In certain embodiments, a formulation or preparation of romidepsin is buffered to prevent the apparent pH from rising above 7.0, more preferably above 6.0. In certain embodiments, the formulation or preparation is buffered to an apparent pH ranging from approximately 4.0 to approximately 6.0.

These and other aspects of the present invention will be further appreciated upon consideration of the following Examples, which are intended to illustrate certain particular embodiments of the invention but are not intended to limit its scope, as defined by the claims.

EXAMPLES

Example 1

Purification of Romidepsin

Purification of Romidepsin by Adsorption Resin

The culture broth of *Chromobacterium violaceum* containing about 400 g of romidepsin (about 600 L; adjusted to pH 2.5 with $H_2SO_4$) is extracted, and the extraction broth is applied to a column packed with SEPABEADS SP850, a non-ionic adsorption resin. Romidepsin (not more than 6 g-romidepsin/L-resin) is bound to the resin with the flow rate of not more than sv=6. After washing with city water (about 3 times resin volume) and 25% aqueous acetone (about 5 times resin volume), elution is carried out with about 65% aqueous acetone and flow rate of not more than sv=4.

Purification of Romidepsin by HP20SS Chromatography

The eluate is diluted with water to produce an aqueous solution (about 75% water content). This solution is applied to a DIAION HP20SS column. This non-ionic adsorption resin adsorbs romidepsin (about 10 g-romidepsin/L-resin) at a flow rate of not more than sv=5. After washing with 25% aqueous acetone (about 0.5 times resin volume) and 40% aqueous acetone (about 4 times resin volume), elution is carried out with 47% aqueous acetone. The eluate is analyzed by reversed phase HPLC (RP-HPLC). The active fractions are combined in an intermediate holding tank.

Replace Aqueous Solvent in Non-Aqueous Solvent with Adsorption Resin

The eluate obtained from the HP20SS column is diluted with water to produce an aqueous solution (about 80% water content). This solution is applied to a DIAION HP20 column. After washing with 20% aqueous acetone, elution is carried out with acetone. The eluate is concentrated in vacuo. After addition of ethyl acetate to the concentrate, the concentrate is further concentrated in vacuo. This step is performed repeatedly.

Purification of Romidepsin with Alumina

The resultant concentrate is dissolved in ethyl acetate (about 6 mg/mL) and applied to an alumina resin column (about 75 g-romidepsin/L-Resin). The column is developed with ethyl acetate (about 2 times alumina volume) and a mixture of acetone and ethyl acetate (0.5-2.0 v/v, about 8 times alumina volume). After addition of acetone to the concentrate, the resultant solution is further concentrated.

Crystallization 1 (Methanol)

The concentrate obtained from the previous step is diluted with methanol and concentrated in vacuo to produce crude romidepsin crystals. The precipitated crystals are collected by filtration.

Crystallization 2 (Acetone/Water)

The crude romidepsin crystals are dissolved in 85% aqueous acetone (about 13 L/kg-crude romidepsin crystals), and precipitated by slow addition of purified water (about 65 L/kg-crude romidepsin crystals) with stirring. The precipitated crystals are collected by filtration and washed with 15% aqueous acetone (about 5 L/kg-crude romidepsin). The wet crystals are dried under vacuum at <−70° C.

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the sub-range are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

What is claimed is:

1. A method of preparing romidepsin, the method comprising the step of isolating romidepsin from a fermentation broth, and the step of purifying romidepsin, wherein at least a portion of the step of purifying is performed at an apparent pH which ranges from approximately 4.0 to approximately 6.0, and wherein romidepsin is greater than 98% monomeric.

2. The method of claim 1, wherein the apparent pH is adjusted by using an organic acid.

3. The method of claim 2, wherein the organic acid is acetic acid.

4. The method of claim 1, wherein the step of purifying comprises purifying by batch chromatography, column chromatography, re-crystallizing, or combinations thereof.

5. A method of preparing romidepsin, the method comprising the step of:
   fermenting a microorganism that produces romidepsin;
   isolating romidepsin from the fermentation broth; and
   purifying romidepsin, wherein at least a portion of the step of purifying is performed at an apparent pH which ranges from approximately 4.0 to approximately 6.0, and wherein romidepsin is greater than 98% monomeric.

6. The method of claim 5, wherein the step of purifying comprises a step of purifying romidepsin by column chromatography.

7. The method of claim 5, wherein the step of purifying comprises a step of purifying romidepsin by re-crystallization.

8. The method of claim 5, wherein the apparent pH is adjusted using an organic acid.

9. The method of claim 8, wherein the organic acid is acetic acid.

10. A method of preparing romidepsin, the method comprising the steps of:
    fermenting an organism that produces romidepsin;
    isolating romidepsin from fermentation broth;
    purifying romidepsin by column chromatography; and
    re-crystallizing romidepsin;
    wherein the step of purifying or re-crystallizing is performed at an apparent pH that ranges from approximately 4.0 to approximately 6.0, and wherein romidepsin is greater than 98% monomeric.

11. The method of claim 10, wherein the step of fermenting comprises fermenting *Chromobacterium violaceum*.

12. The method of claim 10, wherein the step of purifying comprises purifying romidepsin using a non-ionic absorption resin.

13. The method of claim 10, wherein the step of purifying comprises purifying romidepsin using SEPABEDS SP850 styrene-divinylbenzene resin.

14. The method of claim 10, wherein the step of purifying comprises purifying romidepsin using DIAION HP20SS styrene-divinylbenzene resin.

15. The method of claim 10, wherein the step of purifying comprises purifying romidepsin using DIAION HP20 styrene-divinylbenzene resin.

16. The method of claim 10, wherein the step of purifying comprises purifying romidepsin using alumina.

17. The method of claim 10, wherein the step of purifying comprises purifying romidepsin by column chromatography using a column or batch of SEPABEADS SP850 styrene-divinylbenzene resin, followed by a column of DIAION HP20SS styrene-divinylbenzene resin, followed by a column of DIAION HP20 styrene-divinylbenzene resin, and followed by a column of alumina.

18. The method of claim 10, wherein the step of re-crystallizing comprises re-crystallizing romidepsin using methanol.

19. The method of claim 10, wherein the step of re-crystallizing comprises re-crystallizing romidepsin using 85% aqueous acetone.

20. The method of claim 10, wherein the apparent pH is adjusted using an organic acid.

21. The method of claim 20, wherein the organic acid is acetic acid.

22. The method of any one of claim 1, 5, or 10, wherein romidepsin is greater than 99% monomeric.

23. The method of claim 22, wherein romidepsin is greater than 99.9% monomeric.

24. The method of claim 10, wherein the step of re-crystallizing is performed at an apparent pH that ranges from approximately 4.0 to approximately 6.0.

* * * * *

UNITED STATES PATENT AND TRADEMARK OFFICE
CERTIFICATE OF CORRECTION

| | | |
|---|---|---|
| PATENT NO. | : 8,691,534 B2 | Page 1 of 1 |
| APPLICATION NO. | : 11/966258 | |
| DATED | : April 8, 2014 | |
| INVENTOR(S) | : Verdine et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 985 days.

Signed and Sealed this
Eleventh Day of August, 2015

Michelle K. Lee
*Director of the United States Patent and Trademark Office*